United States Patent [19]

Schnur

[11] 4,176,185
[45] Nov. 27, 1979

[54] SPIRO-QUINOLYLHYDANTOINS

[75] Inventor: Rodney C. Schnur, Noank, Conn.

[73] Assignee: Pfizer Inc., New York, N.Y.

[21] Appl. No.: 5,278

[22] Filed: Jan. 22, 1979

[51] Int. Cl.$^2$ .................. C07D 491/20; A61K 31/47; C07D 513/20
[52] U.S. Cl. ..................................... 424/258; 546/18; 546/174; 546/89
[58] Field of Search ......................................... 546/18

[56] References Cited

U.S. PATENT DOCUMENTS

| | | | |
|---|---|---|---|
| 3,876,659 | 4/1975 | Houlihan et al. | 546/18 |
| 4,117,230 | 9/1978 | Sarges | 548/309 |

FOREIGN PATENT DOCUMENTS 1135915 9/1962 Fed. Rep. of Germany .......... 548/309

*Primary Examiner*—Alan L. Rotman
*Assistant Examiner*—Robert T. Bond
*Attorney, Agent, or Firm*—Francis X. Murphy; Charles J. Knuth; Peter C. Richardson

[57] ABSTRACT

Novel spiro-quinolylhydantoin derivatives useful as aldose reductase inhibitors and as therapeutic agents for the treatment of chronic diabetic complications are disclosed. Preferred compounds include spiro[imidazolidin-4,4'-pyrano[3,2-h]quinolin]-2,5-dione and spiro[imidazolidin-4,4'-pyrano[2,3-f]quinolin]-2,5-dione.

17 Claims, No Drawings

SPIRO-QUINOLYLHYDANTOINS

BACKGROUND OF THE INVENTION

This invention relates to novel spiro-quinolylhydantoin derivatives useful in the treatment of certain chronic complications arising from diabetes mellitus, such as diabetic cataracts, retinopathy and neuropathy, to pharmaceutical compositions containing such compounds and to a method of using the compounds.

In the past, various attempts have been made to obtain new and more effective oral anti-diabetic agents. Generally, these efforts have involved synthesis of new organic compounds, particular sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses such as glucose and galactose to the corresponding polyols, such as sorbitol and galacticol, in humans and other animals. In this way, unwanted accumulations of galacticol in the lens of galactosemic subjects and of sorbitol in the lens, peripheral nervous cord and kidney of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel spiro-quinolylhydantoins of the formulae

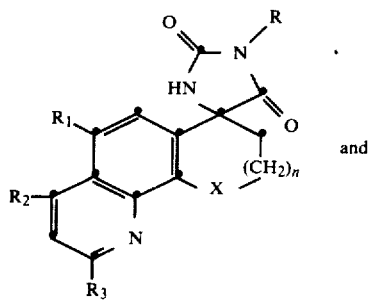

and

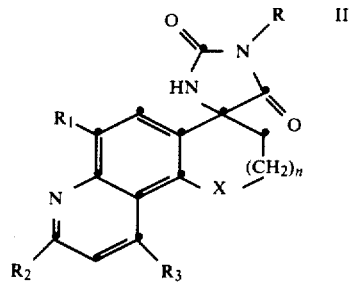

and the base salts thereof with pharaceutically acceptable cations, wherein X is selected from oxygen and sulfur; n is 0, 1 or 2; R is selected from the group consisting of hydrogen, alkyl of 1 to 4 carbon atoms and benzyl; and $R_1$, $R_2$ and $R_3$ are each selected from the group consisting of hydrogen, chloro, bromo, fluoro, alkyl of 1 to 3 carbon atoms and phenyl. Preferably, $R_1$, $R_2$ and $R_3$ are selected from hydrogen, chloro, bromo, fluoro and alkyl of 1 to 3 carbon atoms.

One preferred group of compounds is that wherein the compounds are of formula I, especially wherein X is oxygen and n is 1. Preferably, R, $R_1$, $R_2$ and $R_3$ are each hydrogen.

A further group of compounds of interest is that wherein the compounds are of formula II, especially those wherein X is oxygen and n is 1. Preferably, R, $R_1$, $R_2$ and $R_3$ are each hydrogen.

The present invention further comprises a novel method for the treatment of a diabetic host to prevent or alleviate diabetes-associated complications, such as cataracts, neuropathy or retinopathy which method comprises administering to the host an effective amount of a compound of formula I or II. Preferred compounds employed in this method of treatment are the preferred compounds of formula I and II as described hereinabove.

Also embraced by the present invention are pharmaceutical compositions comprising a pharmaceutically acceptable carrier and a compound of formula I or II in an amount effective to prevent or alleviate diabetes-associated complications, such as cataracts, neuropathy or retinopathy. Preferred compounds for use in such pharmaceutical compositions are those preferred compounds of formulae I and II as described hereinabove.

DETAILED DESCRIPTION OF THE INVENTION

The novel compounds of formulae I and II and X is oxygen can be prepared from appropriately $R_1$, $R_2$, $R_3$-substituted-8-hydroxyquinolines and -5-hydroxyquinolines, respectively. Compounds of formulae I and II wherein X is sulfur can be prepared from the corresponding thiols.

Compounds of formulae I and II wherein n is 1 or 2 may be prepared by reaction of the appropriate hydroxyquinoline with a 3-halo-propionic acid or 4-halo-n-butyric acid, respectively, in the presence of a base, such as an alkali metal hydroxide, generally at a temperature of about 50° C. to 150° C. Preferred acids for this reaction are 3-bromo- and 3-chloro-propionic acid and 4-bromo- and 4-chloro-n-butyric acid. The 3-($R_1$, $R_2$, $R_3$-substituted)-quinolinoxy-propionic acid or 4-($R_1$, $R_2$, $R_3$-substituted)-quinolinoxy-butyric acid produced is then convented to the corresponding ketone of the formula

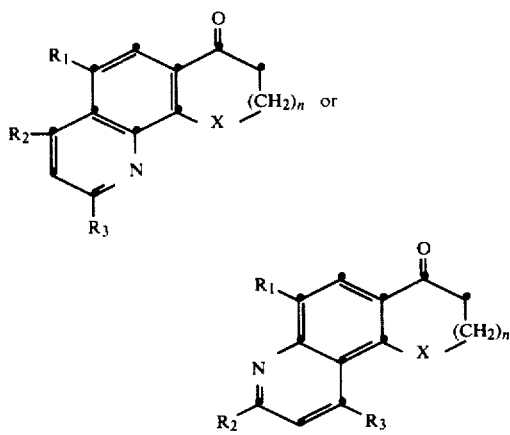

wherein $R_1$, $R_2$, $R_3$ and X are as previously defined and n is 1 or 2, by heating in the presence of a strong acid, such as polyphosphoric acid, sulfuric acid, para-toluene-sulfonic acid and the like, generally at a temperature about 75° C. to 150° C. The reaction may also be effected by reaction of the substituted propionic or butyric acid with thionyl chloride at a temperature of about 10° C. to 40° C. to form the corresponding acid chloride, followed by heating in the presence of a Lewis acid such as aluminum chloride in an inert organic solvent, for example nitrobenzene, nitromethane, and the like.

The ketone of formula III or IV is then condensed with an alkali metal cyanide, such as sodium cyanide or potassium cyanide, and ammonium carbonate to form the desired spiro-quinolylhydantoin of formula I or II, respectively. The reaction is generally conducted in an inert polar organic reaction solvent in which both the reactants and reagents are mutually miscible. Preferred organic solvents include, but are not limited to, cyclic ethers such as dioxane and tetrahydrofuran, lower alkylene glycols such as ethylene glycol and trimethylene glycol, lower alkanols such as methanol, ethanol and isoproponol and N,N-dialkyl-alkanoamides such as N,N-dimethylformamide, N,N-diethylformamide and N,N-dimethylacetamide. In general, the reaction is conducted at a temperature of between about 50° C. and about 150° C., preferably about 90° C. to 130° C., for a period of about 2 hours to about 4 days, depending on the temperature employed. Although the amount of reactants and reagents employed in the reaction can vary to some extent, it is preferably to employ at least a slight molar excess of the alkali metal cyanide reagent with respect to the ketone of formula III or IV in order to obtain the maximum yield. Upon completion of the reaction, the desired product is readily isolated by conventional means, for example by first diluting the reaction mixture with water and then cooling the resultant aqueous solution to room temperature, followed by acidification to afford the desired spiro-quinolylhydantoin in the form of a readily recoverable precipitate.

Compounds of formulae I and II wherein n is 0 may be prepared from the appropriate $R_1$, $R_2$, $R_3$-substituted-8-hydroxyquinoline and $R_1$, $R_2$, $R_3$-substituted-5-hydroxyquinoline, or the thio analogs thereof, by reaction with an acetyl halide, preferably acetyl chloride, to form the corresponding acetate ester. The ester is then heated with a Lewis acid such as aluminum chloride at a temperature of about 80° C. to 120° C. in a reaction inert solvent, for example nitrobenzene, nitromethane and the like, to effect a Fries rearrangement to the corresponding ortho-hydroxy ketones i.e. 7-acetyl-8-hydroxy-quinolines or 5-hydroxy-6-acetyl-quinolines, respectively. Reaction of the carbonyl group of the 7- or 6-acetyl substituent with an alkali metal cyanide in ammonium carbonate under the reaction conditions described hereinabove forms the corresponding 5-(hydroxyquinolyl)-5-methyl-imidazolidin-2,4-diones. The 5-methyl substituent of the imidazole ring is then halogenated by reaction with bromine or chlorine in the presence of a peroxide, such as benzoyl peroxide and the like, or in the presence of light. The halogenation may also be effected by use of N-bromosuccinimide or N-chlorosuccinimide. The halogenation is generally conducted at a temperature of about 0° C. to 100° C. in an inert organic solvent such as chloroform, carbon tetrachloride, tetrachloroethane and the like. Cyclization to the compounds of formulae I and II wherein n is 0 is then effected by elimination of hydrogen halide by reaction with a base, such as an alkali metal hydroxide or alkoxide at a temperature of about 0° C. to 100° C. in an inert organic solvent such as an alkanol of 1 to 4 carbon atoms, dimethylformamide and the like.

Production of compounds of formulae I and II wherein R is alkyl or benzyl is effected by further reacting those compounds where R is hydrogen to introduce the desired substituent, using alkylation reactions well-known in the art. For example, the compounds of formulae I or II wherein R is hydrogen is reacted with an appropriate alkyl halide or benzyl halide, preferably the chloride or bromide, in the presence of a base such as an alkali metal hydroxide, alkoxide or carbonate or a trialkylamine, such as triethylamine. The reaction is generally conducted at a temperature between about 0° C. and 140° C. in a reaction inert solvent such as acetone, a lower alkyl alcohol, dimethyl formamide, an ether such as diethyl ether, tetrahydrofuran, dioxane and the like.

Pharmaceutically acceptable base salts can be readily prepared from compounds of formulae I and II wherein R is hydrogen by conventional methods. Thus, these salts may be readily prepared by treating such spiro-quinolylhydantoins with an aqueous solution of the desired pharmaceutically acceptable cation and evaporating the resulting solution to dryness, preferably under reduced pressure. Alternatively, a lower alkanoic solution of the compound of formulae I or II may be mixed with an alkoxide of the desired metal and subsequently evaporating the solution to dryness. Suitable pharmaceutically acceptable cations for this purpose include, but are not limited to, potassium, sodium, ammonium, calcium and magnesium.

The novel spiro-quinolylhydantoins of this invention are useful as aldose reductase inhibitors, and as such are of therapeutic value in the treatment of chronic complications of diabetes, such as cataracts, retinopathy and neuropathy. As used in the claims and specification hereof, treatment is meant to include both prevention or alleviation of such conditions. The compounds may be administered to a subject in need of treatment by a variety of conventional routes of administration, including orally and parenterally. In general, these compounds will be administered at dosages between about 1 and 250 mg/kg body weight of the subject to be treated per day. However, some variation in dosage will necessarily occur depending on the condition of the subject being treated and the person responsible for administration will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formulae I and II and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes or oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium laurel sulfate and talc are often useful for tableting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes, and if desired emulsifying or suspending agents, together with diluents such as water, ethanol, propylene glycol, glycerin and combinations thereof.

For parenteral administration, solutions of the novel spiro-quinolylhydantoins of formulae I and II in sesame or peanut oil or in aqueous propylene glycol may be employed, as well as sterile aqueous solutions of the corresponding water-soluble alkali metal or alkaline earth metal salts previously described. Such aqueous solutions should be suitably buffered if necessary and the liquid diluent first rendered isotonic with sufficient saline or glucose. These particular aqueous solutions are especially suitable for intraveneous, intramuscular, subcutaneous and intraperitoneal administration. In this connection, the sterile aqueous media employed are all readily available by standard techniques well-known to those skilled in the art. Additionally, it is also possible to administer the spiro-quinolylhydantoin derivatives topically, by use of an appropriate opthalmic solution which may then be administered drop-wise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats.

The present invention is illustrated by the following examples. It will be understood, however, that the invention is not limited to the specific details of these examples.

EXAMPLE 1

3-(8-quinolinoxy)-propionic acid

A solution of 8-hydroxyquinoline (43.5 g, 0.30 mol) (Aldrich) in 150 ml 2 N potassium hydroxide was refluxed while an ice cold solution of 3-chloropropionic acid (36 g, 0.33 mol) (Aldrich) in 165 ml 2 N potassium hydroxide was added over 15 minutes. The pH of the reaction was maintained at pH 10 by addition of 5 N potassium hydroxide during the addition and the subsequent 1.5 hour reflux period. After cooling and filtration the mixture was brought to pH with 6 N hydrochloric acid and extracted with 6×100 ml chloroform. The aqueous layer was acidified to pH 3.8 with 6 N hydrochloric acid and the precipitate thus formed was filtered and washed thoroughly with water, to yield 3-[8-quinolinoxy]-propionic acid (16.12 g, 25% yield), m.p. 211°–213° C.

EXAMPLE 2

Pyrano[3,2-h]quinolin-4-one

A solution of 3-(8-quinolinoxy)-propionic acid (2.17 g, 0.010 mol) in 10 ml of thionyl chloride was kept for 1 hour at 20° C. then evaporated in vacuo to a residue. This was suspended in 50 ml of nitrobenzene and aluminum chloride (1.50 g, 0.011 mol) was added. The mixture was heated to 100° C. for 1 hour, cooled and poured over 200 ml 1 N hydrochloric acid and 100 ml ice. The organic layer was separated and washed with 3×50 ml 6 N hydrochloric acid. The combined aqueous fractions were washed with 3×100 ml ether then basified with 6 N sodium hydroxide and extracted with 2×200 ml methylene chloride. This organic phase was dried over magnesium sulfate, decolorized with Darco, filtered, and evaporated in vacuo to a yellow solid, pyran[3,2-h]quinolin-4-one (450 mg, 23% yield). Recrystallization twice from toluene gave material of m.p. 177.5°–180.0° C.

EXAMPLE 3

Spiro[imidazolidin-4,4'-pyrano[3,2-h]quinolin]-2,5-dione

A solution of 0.500 g (2.51 mmol) of potassium cyanide and 0.280 g (4.27 mmol) of ammonium carbonate in 1.5 ml water was added to a solution of 130 mg (0.65 mmol) of pyrano[3,2-h]quinolin-4-one in 1.5 ml of ethanol at 60° C. The reaction mixture was held at this temperature for 72 hours then added to 20 ml of water and boiled for 20 minutes. The basic mixture was extracted with 3×50 ml chloroform and the mixture was acidified with 1 N hydrochloric acid. The solid obtained after filtration and drying in vacuo (96 mg) was twice recrystallized from ethanol yielding spiro[imidazolidin-4,4'-pyrano[3,2-h]quinolin]-2,5-dione, (36.0 mg), m.p. 305° C. (dec).

EXAMPLE 4

3-(5-quinolinoxy)-propionic acid

A solution of 5-hydroxyquinoline (4.91 g, 0.0340 mole) (Aldrich) in 17 ml 2 N potassium hydroxide was refluxed while an ice cold solution of 3-chloropropionic acid (4.05 g, 0.0373 mole) (Aldrich) in 18.6 ml 2 N potassium hydroxide was added during 1 minute. The pH was maintained at pH 9.5 by addition of 2 N potassium hydroxide. After 10 minutes, the mixture was allowed to come to room temperature and stirred for 16 hours. The pH of the solution was adjusted to pH 3.8 and the mixture evaporated in vacuo to a residue which was column chromatographed on silica gel by elution with 4:1 ethyl acetate:methanol. Material of $R_f$=0.45 (thin layer chromatography using 1:1 ethyl acetate:methanol) was obtained and recrystallized from water; m.p. 217°–219° C.

EXAMPLE 5

Pyrano[2,3-f]quinolin-4-one

Polyphosphoric acid (26 ml) was heated at 90°–95° C. and stirred while 3-(5-quinolinoxy)-propionic acid (2.60 g, 0.0120 mole) was added in small portions. After heating for 2 hours the mixture was poured into 200 ml ice water, basified to pH 10 with concentrated ammonium hydroxide and extracted with 3×200 ml ethyl acetate. The combined organic plasma were dried over magnesium sulfate, filtered, and evaporated in vacuo to a solid, which were recrystallized from toluene, m.p. 146°–147° C.

EXAMPLE 6

Spiro[imidazolidin-4,4'-pyrano[2,3-f]quinolin]-2,5-dione

The title compound was prepared from pyrano[2,3-f]quinolin-4-one in a manner analogous to that described in Example 3 except that the mixture was heated for 48 hours with 3.6 equivalents of potassium cyanide; (172 mg. 64% yield), m.p. 330° C.

EXAMPLE 7

5-(5'-chloro-8-hydroxy-7'-quinolyl)-5-methylimidazolidin-2,4-dione

5-Chloro-8-hydroxy-7-quinolyl methyl ketone (U.S. Pat. No. 3,113,135) (1 mmol), potassium cyanide (2 mmol), and ammonium carbonate (4 mmol) are heated at 60° in 5 ml of 50% aqueous ethanol. After 3 days 20 ml of water is added and the mixture is boiled for 20 minutes. The basic aqueous mixture is extracted with chloroform then acidified with 1N HCl to pH 6. The solid is collected by filtration washed with water and dried in vacuo.

EXAMPLE 8

5-Chloro-spiro[furo[3,2-h]quinolin-3,4'-imidazolidin]-2',5'-dione

The compound of Example 7 (1 mmol), a catalytic amount of dibenzoyl peroxide, and chlorine (1 mmol) are stirred in tetrachlorethane. After the reaction is complete the organic layer is washed with sodium bicarbonate, dried over magnesium sulfate, filtered, and evaporated in vacuo. The residue is dissolved in dimethylformamide and is treated with potassium t-butoxide (1 mmol). The product is isolated by partitioning the reaction mixture between ethyl acetate and water. The organic layer is dried and evaporated to a residue which is crystallized from alcohol.

EXAMPLE 9

The compounds of Examples 3 and 6 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-4}$ M are expressed as percent inhibition of enzyme activity.

| Compound of | % Inhibition at $10^{-4}$M |
|---|---|
| Example 3 | 75 |
| Example 6 | 94 |

EXAMPLE 10

The compounds of Examples 3 and 6 were tested for their ability to reduce or inhibit sorbitol accumulation in the sciatic nerve of streptozotocinized (i.e. diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented below in terms of percent inhibition (%) afforded by the test compound as compared to the case where no compound was administered (i.e. the untreated animal where sorbitol levels normally rise from approximately 50–100 mM/g. tissue to as high as 400 mM/g. tissue in the 27-hour test period):

| | % Inhibition | |
|---|---|---|
| Compound of | 1.5 mg/kg | 10 mg/kg |
| Example 3 | 27 | — |
| Example 6 | — | 92 |

What is claimed is:
1. A compound selected from the formulae

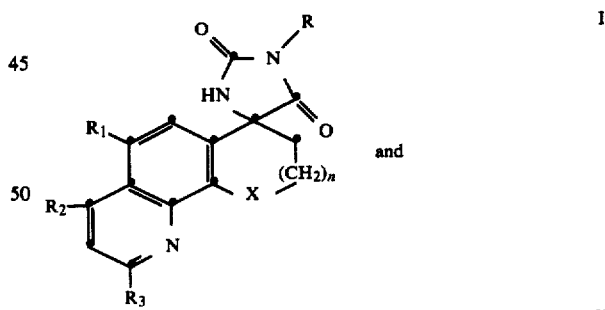

and

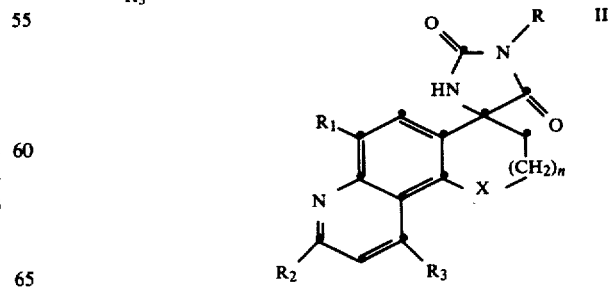

and the base salts thereof with pharmaceutically acceptable cations, wherein

X is selected from oxygen and sulfur;

n is zero, one or two;

R is selected from the group consisting of hydrogen, alkyl of 1 to 4 carbon atoms and benzyl;

and $R_1$, $R_2$ and $R_3$ are each selected from the group consisting of hydrogen, chloro, bromo, fluoro and alkyl of 1 to 3 carbon atoms.

2. A compound of claim 1, formula I.

3. A compound of claim 2 wherein X is oxygen.

4. A compound of claim 3 wherein n is one.

5. A compound of claim 4 wherein R is hydrogen.

6. A compound of claim 5 wherein $R_1$, $R_2$ and $R_3$ are each hydrogen.

7. A compound of claim 1, formula II.

8. A compound of claim 7 wherein X is oxygen.

9. A compound of claim 8 wherein n is one.

10. A compound of claim 9 wherein R is hydrogen.

11. A compound of claim 10 wherein $R_1$, $R_2$ and $R_3$ are each hydrogen.

12. A pharmaceutical composition comprising a pharmaceutically-acceptable carrier and a compound of claim 1 in an amount effective for the treatment of diabetic cataracts, neuropathy or retinopathy.

13. A pharmaceutical composition of claim 12 wherein said compound is of formula I, X is oxygen, n is one, R, $R_1$, $R_2$ and $R_3$ are each hydrogen.

14. A pharmaceutical composition of claim 12 wherein said compound is of formula II, X is oxygen, n is one, R, $R_1$, $R_2$ and $R_3$ are each hydrogen.

15. A method of treating a diabetic host for diabetic cataracts, neuropathy or retinopathy which comprises administering to said host an effective amount of a compound of claim 1.

16. A method according to claim 15 wherein said compound is of formula I, X is oxygen, n is one, R, $R_1$, $R_2$ and $R_3$ are each hydrogen.

17. A method according to claim 15 wherein said compound is of formula II, X is oxygen, n is one, R, $R_1$, $R_2$ and $R_3$ are each hydrogen.

* * * * *